United States Patent
Parks

(10) Patent No.: US 8,902,436 B1
(45) Date of Patent: Dec. 2, 2014

(54) CHIRAL SLAB THICKNESS MEASUREMENT USING WEAK VALUE AMPLIFICATION

(75) Inventor: Allen D. Parks, Spotsylvania, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 720 days.

(21) Appl. No.: 13/134,432

(22) Filed: Jun. 27, 2011

(51) Int. Cl.
*G01B 11/06* (2006.01)
*G01B 1/00* (2006.01)
*G01N 21/21* (2006.01)
*G01N 21/01* (2006.01)

(52) U.S. Cl.
CPC ........ *G01B 11/06* (2013.01); *G01N 2021/0106* (2013.01); *G01N 21/21* (2013.01); *G01B 1/00* (2013.01)
USPC .......................................................... 356/632

(58) Field of Classification Search
CPC .......... G01S 11/12; G01B 1/00; G01B 11/06; G01N 21/21; G01N 2021/0106
USPC .......................................................... 356/632
See application file for complete search history.

(56) References Cited

U.S. PATENT DOCUMENTS

| | | | |
|---|---|---|---|
| 5,956,147 A * | 9/1999 | Jellison et al. | 356/369 |
| 5,989,461 A | 11/1999 | Coates et al. | 252/585 |
| 6,671,293 B2 * | 12/2003 | Kopp et al. | 372/6 |
| 6,678,297 B2 * | 1/2004 | Kopp et al. | 372/43.01 |
| 6,925,230 B2 | 8/2005 | Kopp et al. | 385/37 |
| 2001/0036212 A1* | 11/2001 | Kopp et al. | 372/43 |

FOREIGN PATENT DOCUMENTS

JP   2003057147 A  *  2/2003

OTHER PUBLICATIONS

M. Pfeifer and P. Fischer, "Weak value amplified optical activity measurements," Opt. Express 19, 16508-16517 (2011).*

(Continued)

*Primary Examiner* — Ari M Diacou
(74) *Attorney, Agent, or Firm* — Gerhard W. Thielman, Esq.

(57) ABSTRACT

A method is provided for determining a thickness L of a chiral slab that refracts incident linearly polarized light into right (+) and left (−) circularly polarized beams. The method includes disposing the slab in an achiral medium, determining values of translation coefficients $\gamma_\pm$, determining values for refraction angle differences $(\theta_+ - \theta_-)$, selecting pre- and post selection states $|\psi_i\rangle$ and $|\psi_j\rangle$, projecting an emitted light beam through said achiral medium into the chiral slab a small established angle of incidence $\theta_0$, varying slab egress phase angles $\beta_\pm$, determining said pointer mean value $\langle x \rangle$, calculating weak value $A_w$, and calculating the thickness as $$L = \frac{\langle x \rangle}{\mathrm{Re}A_w}.$$

The achiral medium has an established index of refraction $n_0$. The translation coefficients $\gamma_\pm$ establish refraction translation differences $(\gamma_+ - \gamma_-)$. The pre-selection state $|\psi_i\rangle$ establishes pre-selection alignment angle to satisfy $\Phi = \pi/4$. The post-selection state $|\psi_j\rangle$ establishes post-selection alignment angle to satisfy $\chi = \Phi - \epsilon$ and $0 < \epsilon \ll 1$. The slab egress phase angles $\beta_\pm$ are adjusted until pointer mean value $\langle x \rangle$ attains one of a maximum for $(\gamma_+ - \gamma_-) > 0$ or else a minimum for $(\gamma_+ - \gamma_-) < 0$. In various exemplary embodiments, the weak value is approximated as $$A_w \approx \frac{\gamma_+ - \gamma_- + 2\epsilon\gamma_-}{2\sin\epsilon} \approx \frac{\gamma_+ - \gamma_-}{2\epsilon}.$$

16 Claims, 1 Drawing Sheet

(56) References Cited

OTHER PUBLICATIONS

M. Schubert, C. Cramer, J. Woollam, C. Herzinger, B. Johs, H. Schmiedel, and B. Rheinländer, "Generalized transmission ellipsometry for twisted biaxial dielectric media: application to chiral liquid crystals," J. Opt. Soc. Am. A 13, 1930-1940 (1996). http://dx.doi.org/10.1364/JOSAA.13.001930.*

A. Ghosh et al., "Chiral Molecules Split Light: Reflection and Refraction in a Chiral Liquid", *Phys. Rev. Lett.* 97, 173002 (2006) http://journals.aps.org/prl/pdf/10.1103/PhysRevLett.97.173002.

C. Sabah et al., "Mirrors with Chiral Slabs", *J. Optoelectronics and Advanced Materials* 8, 5 (2006). http://joam.inoe.ro/arhiva/pdf8_5/5Sabahl.pdf.

S. Uçkun et al., "Three concentric rings as frequency selective surfaces on isotropic chiral slabs", *J. of Optoelectronics and Advanced Materials* 8, 1, 345-349. http://www.inoe.ro/JOAM/pdf$8_{13}$ 1/Uckun.pdf.

S. He et al., "Wave Propagation in a Stratified Chiral Slab with Multiple Discontinuities", *Progress in Electromagnetics Research (PIER)* 9, 137-156 (1994). http://www.jpier.org/PIER/pier09/08.9309100.pdf.

F. Guérin, "Microwave Chiral Materials: A Review of Experimental Studies and some results on composites . . . ", *PIER* 9, 219-263 (1994). http://www.jpier.org/PIER/pier09/11.9301014.pdf.

J. C. da S. Laacava, "An Alternative Formulation for Guided Electromagnetic Fields in Grounded Chiral Slabs", *PIER* 16, 285-304 (1997). http://www.jpier.org/PIER/pier16/11.961011p.Lacava.L.pdf.

W. T. Dong et al., "Goos-Hänchen Shift at the Surface of Chiral Negative Refractive Media", *PIER* 90, 255-268 (2009). http://www.jpier.org/PIER/pier90/17.08122002.pdf.

J. F. Dong, "Wave Modes in Chiral Negative Refraction Grounded Slab Waveguides", *PIER* 95, 153-166 (2009). http://www.jpier.org/PIER/pier95/10.09062604.pdf.

J. Lekner, "Properties of a chiral slab waveguide", *Pure Appl. Opt.* 6 (1997) 373-384. http://www.victoria.ac.nz/scps/staff/pdf/Properties_of_a_chiral_slab_waveguide.pdf.

S. Bassiri et al., "Electromagnetic wave propagation through a dielectric-chiral interface and through a chiral slab", *J. Opt. Soc. Am. A* 5, 9 (1988). http://authors.library.caltech.edu/11143/1/BASjosaa88.pdf.

G. Öğücü et al., "A Uniaxial Chiral Slab Backed by Soft and Hard Surfaces Used as a Polarization Transformer", $8^{th}$ *Int'l Conf. on Electromagnetics of Complex Media* (2000). http://www.dtic.mil/cgi-bin/GetTRDoc?Location=U2&doc=GetTRDoc.pdf&AD=ADP011645.

A. Lakhtakia, "Time-Harmonic Dyadic Green's Functions for Reflection and Transmission by a Chiral Slab", *AEÜ* 47, 1 (1993). http://www.esm.psu.edu/~axl4/lakhtakia/documents/No186(AEUe).pdf.

A. Lakhtakia, "Narrowband and ultranarrowband filters with electro-optic structurally chiral materials", *Asian J. of Physics* 15, 3 275-282 (2006). http://www.esm.psu.edu/~axl4/lakhtakia/Documents/No565(AJP).

V. Demir et al., "FDTD Formulation for Dispersive Chiral Media Using the Z Transform Method", *IEEE Transactions on Antennas and Propagation* 53, 10 (2005). http://www.ee.olemiss.edu/atef/journals/74-FDTD%20Formulation%20for%20.pdf.

Y. Y. Huang et al., "Large positive and negative lateral shifts near pseudo-Brewster dip . . . " *Optics Express* 19, 2 (2011). http://www.ece.nus.edu.sg/stfpage/eleqc/GHShift_chiral_OE2011.pdf.

R. Zhao et al., "Chiral metameterials: retrieval of the effective parameters with and without substrate", *Optics Express* 18, 14 (2010). http://cmp.physics.iastate.edu/soukoulis/publications/20092010/360.pdf.

S. J. Orfanidis, *Electromagnetic Waves and Antennas*, 2002 §§3.1-3.3 (pp. 76-81). http://www.compuland.com.br/helio/mestrado/S.%20J.%20Orfanidis%20-%20Electromagnetic%20Waves%20and%20Antennas.pdf.

\* cited by examiner

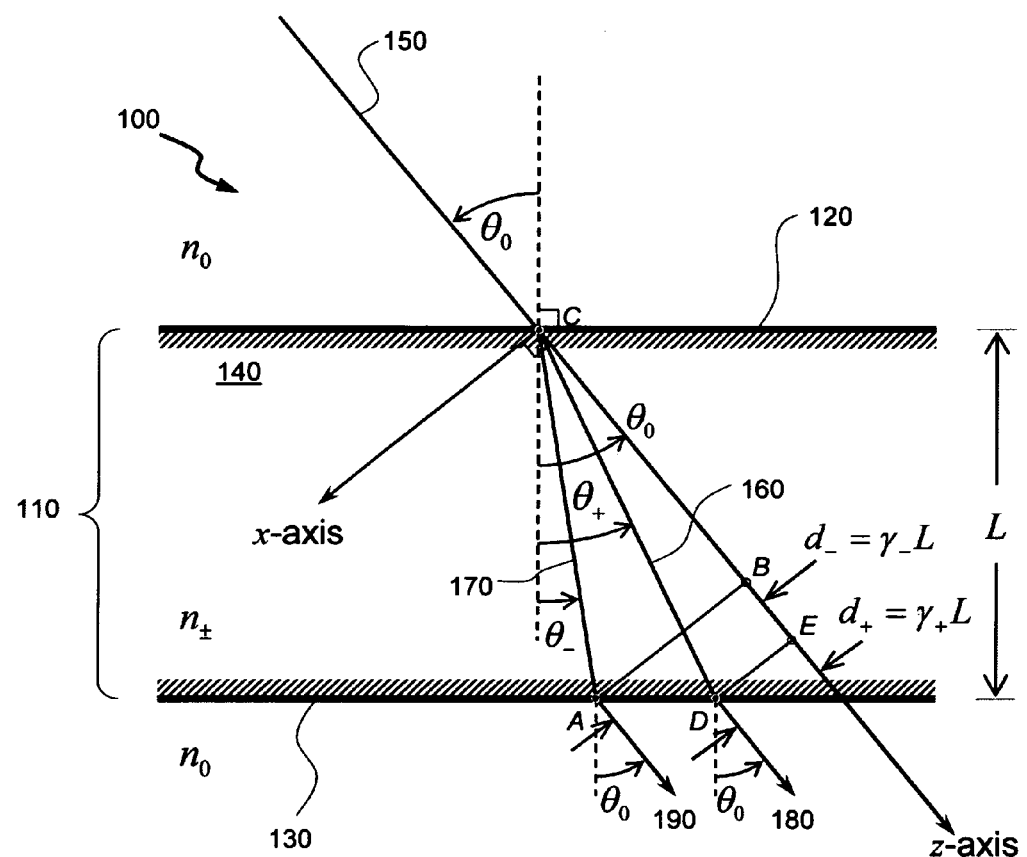

CHIRAL SLAB THICKNESS MEASUREMENT USING WEAK VALUE AMPLIFICATION

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to thickness measurement of a thin transparent chiral slab. In particular, this invention relates to physical characterization of a planar chiral medium using weak value amplification of photons passing therethrough.

A chiral medium exhibits an asymmetry in optical response, either for reflection or refraction. Such media can be used in a variety of applications, including biasing waveguides. Such capabilities can facilitate designs for radar energy absorption and electromagnetic shielding. However, conventional techniques for measuring thicknesses of a thin transparent chiral slab entail difficulties under circumstances of limited accessibility.

SUMMARY

Conventional thickness measurement techniques for chiral slabs yield disadvantages addressed by various exemplary embodiments of the present invention. Various exemplary embodiments provide a method determining a thickness L of a chiral slab using its refraction of linearly polarized light into right (+) and left (−) circular polarized beams.

The method includes disposing the slab in an achiral medium, determining values of translation coefficients $\gamma_\pm$, determining values for refraction angle differences $(\theta_+ - \theta_-)$, selecting pre- and post selection states $|\psi_i\rangle$ and $|\psi_f\rangle$, projecting an emitted light beam through said achiral medium into the chiral slab, varying slab egress phase angles $\beta_\pm$, determining said pointer mean value $\langle x \rangle$, calculating weak value $A_w$, and calculating the thickness as $$L = \frac{\langle x \rangle}{\text{Re} A_w}.$$

In various exemplary embodiments, the light approaches the achiral medium with an angle of refraction $n_0$ from an index of incidence $\theta_0$ to the normal of the surface of the chiral medium. The translation coefficients $\gamma_\pm$ establish a refraction translation difference $(\gamma_+ - \gamma_-)$. The pre-selection state $|\psi_i\rangle$ establishes pre-selection linear polarization angle to satisfy $\Phi = \pi/4$.

In various exemplary embodiments, the post-selection state $|\psi_f\rangle$ establishes post-selection alignment angle to satisfy $\chi = \Phi - \epsilon$ and $0 < \epsilon \ll 1$. The slab egress phase angles $\beta_\pm$ are adjusted until the pointer mean value $\langle x \rangle$ attains one of a maximum for $(\gamma_+ - \gamma_-) > 0$ or else a minimum for $(\gamma_+ - \gamma_-) < 0$. In alternative exemplary embodiments, the weak value $A_w$ of a displacement operator $\hat{A}$ that describes the process can be approximated as $$A_w \approx \frac{\gamma_+ - \gamma_- + 2\epsilon\gamma_-}{2\sin\epsilon} \approx \frac{\gamma_+ - \gamma_-}{2\epsilon}.$$

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which:

FIGURE is a diagram view of a diagram of polarized optical paths through a chiral slab.

DETAILED DESCRIPTION

In accordance with a presently preferred embodiment of the present invention, the components, process steps, and/or data structures may be implemented using various types of operating systems, computing platforms, computer programs, and/or general purpose machines. In addition, those of ordinary skill in the art will readily recognize that devices of a less general purpose nature, such as hardwired devices, or the like, may also be used without departing from the scope and spirit of the inventive concepts disclosed herewith. General purpose machines include devices that execute instruction code. A hardwired device may constitute an application specific integrated circuit (ASIC) or a floating point gate array (FPGA) or other related component.

This disclosure explains a process to use weak value amplification to measure the thickness of a thin parallel slab of transparent chiral material. Such measurements can be made using either classically intense laser light or single photon streams if minimal intrusiveness is required.

An interface surface is naturally formed between an achiral medium and a chiral medium. A linearly polarized beam of photons incident to the interface from the achiral into the chiral media refracts as two distinct circularly polarized photon beams, as reported by A. Ghosh et al. "Chiral Molecules Split Light: Reflection and Refraction in a Chiral Liquid" in *Phys. Rev. Lett.* 97 173002 (2006). See http://arxiv.org/PS_cache/physics/pdf/0608/0608120v1.pdf for details.

The FIGURE depicts an optical diagram 100 exhibiting a thin chiral slab 110 having a thickness L, being bounded by incident and egress interface surfaces 120 and 130 containing a chiral medium 140 therebetween having indices of refraction $n_\pm$. The subscripts plus (+) and minus (−) respectively correspond to right and left circular polarized refraction. An achiral medium surrounds the chiral slab 110 and has an index of refraction of $n_0$.

A monochromatic linearly polarized coherent laser beam 150 of wavelength $\lambda$ enters the slab 110 at an angle of incidence of $\theta_0$, which defines a z-axis and an x-axis. The incident beam 150 forms either a classically intense continuum or a stream of single photons. At the first (incident) interface 120, the incident beam 150 refracts into a pair of right and left circularly polarized refracted beams 160 and 170, respectively. The right circularly polarized beam 160 refracts at an angle of $\theta_+$, whereas the left circularly polarized beam 170 refracts at an angle of $\theta_-$, both angles from the normal to the interface.

Upon exiting the slab 110 into the achiral medium, the right refracted beam 160 returns to the angle of incidence of $\theta_0$ as right exit beam 180; and the left refracted beam 170 also returns to the same incidence angle $\theta_0$ as left exit beam 190. The right and left exit beams 180 and 190 are parallel to the z-axis and displaced therefrom by respective distances $d_+$ and $d_-$.

Consider the diagram 100, which depicts a classically intense beam 150 or alternatively a stream of single photons, if minimal intrusiveness is required. The beam 150 transmits as monochromatic coherent laser light through an achiral medium having index of refraction $n_0$. The thin transparent slab 110 of chiral material has thickness L and is characterized by the indices of refraction $n_\pm$ in which subscripts plus (+) and minus (−) respectively correspond to right and left circular polarized light.

The beam 150 reaches the first interface 120 of the slab 110 at an incident angle $\theta_0$. In passage through the chiral medium 140, the beam 150 divides into two beams with refraction angles $\theta_\pm$ corresponding to the right and left circular polarizations. The relationship between these quantities is given by Snell's law.

$$n_0 \sin\theta_0 = n_\pm \sin\theta_\pm. \quad (1)$$

Each refracted photon beam 160 and 170 follows a straight line as it transits the chrial material 140 in the slab 110. Due to the rotary power of the chiral material 140, the beams 160 and 170 acquire phase angles $\alpha_\pm$ by the transit. These beams 160 and 170 then refract through the second (egress) interface 130 back into the achiral medium.

Snell's law in eqn. (1) provides that the refraction angles for each of the emergent beams 180 and 190 be $\theta_0$, i.e., they each emerge from second interface 130 of the slab 110 parallel to the laser's incident beam 150. However, these beams 180 and 190 are displaced from its direction of propagation by distinct distances $d_\pm$. More specifically, if the photon distribution of the incident beam 150, which propagates in the z-direction of the laboratory reference frame as shown in the diagram 100, has a Gaussian distribution in the x-direction with mean value at x=0, then each of the two parallel emergent beams 180, 190 exhibit displaced Gaussian distributions in the x-direction with mean values at $x=d_\pm$.

Using the FIGURE and simple trigonometry, one can determine the displacements $d_\pm$. Perpendicular angles $\angle ABC$ and $\angle DEC$, in which displacements $d_+$ and $d_-$ form respective segments $\overline{AB}$ and $\overline{DE}$, yield displacement relations:

$$d_\pm = h_\pm \sin(\theta_0 - \theta_\pm), \quad (2)$$

where $$h_\pm = \frac{L}{\cos\theta_\pm} \quad (3)$$

are the lengths of each associated hypotenuse as respective segments $\overline{AC}$ (along beam 170) and $\overline{DC}$ (along beam 160). Thus displacements can be expressed in relation to the thickness L as:

$$d_\pm = L\gamma_\pm, \quad (4)$$

such that $\gamma_\pm$ represents refraction translation coefficients for the right and left polarizations as in the expression:

$$\gamma_\pm = \sin\theta_0 - \cos\theta_0 \tan\theta_\pm. \quad (5)$$

The above process can be described from a quantum mechanical perspective using the mean of the x-direction photon distribution as a measurement pointer. This description is valid for both the single photon and classical intensity perspectives. In particular, Hermitean operators $\hat{A}$ and $\hat{B}$ can be constructed and used to form an interaction Hamiltonian that defines the evolutionary dynamics of the process.

Let kets $|+\rangle$ and $|-\rangle$ be the right and left circular polarization eigen-states, respectively, of the photon circular polarization operator $\hat{\sigma}$. These eigen-states obey the eigenvalue equation:

$$\hat{\sigma}|\pm\rangle = \pm|\pm\rangle \quad (6)$$

and have the orthogonality properties:

$$\langle\pm|\pm\rangle = 1 \text{ and } \langle\pm|\mp\rangle = 0. \quad (7)$$

Then the Hermitean operators $\hat{A}$ (for displacement) and $\hat{B}$ (for phase rotation) can be defined as:

$$\hat{A} = \gamma_+|+\rangle\langle+|+\gamma_-|-\rangle\langle-| \quad (8)$$

and $$\hat{B} = \alpha_+|+\rangle\langle+|+\alpha_-|-\rangle\langle-|, \quad (9)$$

where translation coefficients $\gamma_\pm$ and phase angles $\alpha_\pm$ represent eigenvalues of their respective operators. The associated interaction Hamiltonian can then be expressed as:

$$\hat{H} = [L\hat{A}\hat{p}_x - \hbar\hat{B}]\delta(t-t_0), \quad (10)$$

where $\hbar$ is the reduced Planck's constant, and for small L the Dirac delta function $\delta(t-t_0)$ models the refraction effectively as an impulsive interaction between a photon of the beam 150 and the first interface 120 at time $t_0$.

Here $\hat{p}_x$ is the measurement pointer's x-component momentum operator conjugate to its x-position operator $\hat{x}$, and one can assume that the interaction between a photon and the chiral material 140 in the slab 110 is impulsive and occurs at time $t_0$. Operator $\hat{A}$ accounts for the displacements of the initial pointer distribution, the thickness L represents the associated coupling constant for the interaction, and $\hat{B}$ accounts for the circular polarization state phase angles $\alpha_\pm$ induced by the rotary power of the chiral material. One can note that:

$$[\hat{A}, \hat{B}] = 0 \quad (11)$$

and that $|\pm\rangle$ are eigenstates of both $\hat{A}$ and $\hat{B}$.

If the ket $|\psi_i\rangle$ is an initial photon polarization state, i.e., the pre-selected state resulting from an unshown pre-selection filter, and ket $|\phi\rangle$ is the initial (Gaussian) pointer state defined by the beam 150, then the initial state of the combined pre-selected system and measurement pointer prior to the inter-action is the tensor product $|\psi_i\rangle|\phi\rangle$. Immediately after the measurement's impulsive interaction the combined system is in the state:

$$|\Psi\rangle = e^{-\frac{i}{\hbar}\int \hat{H} dt}|\psi_i\rangle|\phi\rangle = e^{-\frac{i}{\hbar}L\hat{A}\hat{p}_x}e^{i\hat{B}}|\psi_i\rangle|\phi\rangle, \quad (12)$$

where $i \equiv \sqrt{-1}$ is the imaginary unit, and use has been made of the facts that $$\int \delta(t-t_0)dt \leq 1, \quad (13)$$

and $$[\hat{A}\hat{p}_x, \hat{B}] = 0. \quad (14)$$

Now let $|\psi_i\rangle$ be the polarization state expressed as:

$$|\psi_i\rangle = a|+\rangle + b|-\rangle, \quad (15)$$

with a and b representing pre-selection state polarization coefficients. Then rewrite eqn. (12) as the state of the combined system:

$$|\Psi\rangle = e^{-\frac{i}{\hbar}L\hat{A}\hat{p}_x}e^{i\hat{B}}(a|+\rangle + b|-\rangle)|\varphi\rangle. \quad (16)$$

Because the $n^{th}$ power of operator $\hat{B}$ has the sum:

$$\hat{B}^n = \alpha_+^n |+\rangle\langle+| + \alpha_-^n |-\rangle\langle-| \text{ such that } n=0, 1, 2,\ldots, \quad (17)$$

then:

$$e^{\frac{i}{\hbar}\hat{B}} = \sum_{n=0}^{\infty} \frac{(i\hat{B})^n}{n!} \quad (18)$$

$$= \sum_{n=0}^{\infty} \frac{(i\alpha_+)^n}{n!}|+\rangle\langle+| + \sum_{n=0}^{\infty} \frac{(i\alpha_-)^n}{n!}|-\rangle\langle-|$$

$$= e^{i\alpha_+}|+\rangle\langle+| + e^{i\alpha_-}|-\rangle\langle-|,$$

so that eqn. (12) becomes:

$$|\Psi\rangle = e^{-\frac{i}{\hbar}L\hat{A}\hat{p}_x}(ae^{i\alpha_+}|+\rangle + be^{i\alpha_-}|-\rangle). \quad (19)$$

More simply, this results directly from the fact relating the operator to its phase angles as:

$$\hat{B}|\pm\rangle = \alpha_\pm|\pm\rangle. \quad (20)$$

In addition, because $$[\hat{A},\hat{p}_x]=0, \quad (21)$$

and the $n^{th}$ power of operator $\hat{A}$ has the sum:

$$\hat{A}^n = \gamma_+^n |+\rangle\langle+| + \gamma_-^n |-\rangle\langle-| \text{ such that } n=0, 1, 2,\ldots \quad (22)$$

can be related by the exponential relation:

$$e^{\frac{i}{\hbar}L\hat{A}\hat{p}_x} = \sum_{n=0}^{\infty} \frac{\left[-\frac{i}{\hbar}L\hat{A}\hat{p}_x\right]^n}{n!} \quad (23)$$

$$= \sum_{n=0}^{\infty} \frac{\left[-\frac{i}{\hbar}L\hat{p}_x\gamma_+\right]^n}{n!}|+\rangle\langle+| + \sum_{n=0}^{\infty} \frac{\left[-\frac{i}{\hbar}L\hat{p}_x\gamma_-\right]^n}{n!}|-\rangle\langle-|$$

$$= e^{\frac{i}{\hbar}L\hat{p}_x\gamma_+}|+\rangle\langle+| + e^{\frac{i}{\hbar}L\hat{p}_x\gamma_-}|-\rangle\langle-|.$$

In other words, this results directly from the fact relating the operator to its refraction translators as:

$$\hat{A}|\pm\rangle = \gamma_\pm|\pm\rangle. \quad (24)$$

Using the closure relation:

$$\hat{1} = \int |x\rangle dx \langle x| \quad (25)$$

in eqn. (19) yields the following expression for the combined state $|\Psi\rangle$ in terms of the x-representation of the measurement pointer:

$$|\Psi\rangle = \quad (26)$$

$$ae^{i\alpha_+}|+\rangle\int \langle x|e^{-\frac{i}{\hbar}L\gamma_+\hat{p}_x}|\varphi\rangle|x\rangle dx + be^{i\alpha_-}|-\rangle\int \langle x|e^{-\frac{i}{\hbar}L\gamma_-\hat{p}_x}|\varphi\rangle|x\rangle dx.$$

One can recognize that defining eqn. (23) such that:

$$e^{-\frac{i}{\hbar}L\gamma_\pm\hat{p}_x} \equiv \hat{S}(L\gamma_\pm) = \hat{S}(d_\pm), \quad (27)$$

as x-direction translation operators $\hat{S}$ enables the system state in eqn. (26) in the x-representation to be rewritten as:

$$\langle x|\Psi\rangle = ae^{i\alpha_+}|+\rangle\langle x|\hat{S}(d_+)|\varphi\rangle + be^{i\alpha_-}|-\rangle\langle x|\hat{S}(d_-)|\varphi\rangle \quad (28)$$

$$= ae^{i\alpha_+}|+\rangle\varphi(x - d_+) + be^{i\alpha_-}|-\rangle\varphi(x - d_-),$$

where use has been made of the facts that:

$$\langle x|x'\rangle = \delta(x-x'), \quad (29)$$

and $$\int f(x')\delta(x-x')dx = f(x). \quad (30)$$

Then the associated pointer state distribution in the x-direction is:

$$|\langle x|\Psi\rangle|^2 = |a|^2|\varphi(x-d_+)|^2 + |b|^2|\varphi(x-d_-)|^2, \quad (31)$$

corresponding to two Gaussian distributions with means displaced by $d_\pm$ along the x-axis of the laboratory reference frame. If the ket $|\psi_f\rangle$, expressed by:

$$|\psi_f\rangle = qe^{i\beta_+}|+\rangle + re^{i\beta_-}|-\rangle, \quad (32)$$

represents a final photon polarization state, i.e., the post-selected state resulting from an unshown post-selection filter with q and r denoting post-selection polarization coefficients, then the resulting measurement pointer state $|\Phi\rangle$ in terms of the laboratory frame's x-representation is:

$$|\Phi\rangle = \langle\psi_f|\Psi\rangle = aq^* e^{i(\alpha_+-\beta_+)}\int \langle x|\hat{S}(d_+)|\varphi\rangle |x\rangle dx + br^* e^{i(\alpha_--\beta_-)}\int \langle x|\hat{S}(d_-)|\varphi\rangle |x\rangle dx, \quad (33)$$

in which asterisk superscripts denote complex conjugates of q and r.

A weak measurement of $\hat{A}$ occurs when the thickness L is sufficiently small and the pointer position uncertainty $\Delta x$ is much larger than $d_\pm$. In this case the associated post-selected pointer state is:

$$|\Phi\rangle = \langle\psi_f|e^{-\frac{i}{\hbar}L\hat{A}\hat{p}_x}e^{i\hat{B}}|\psi_i\rangle|\varphi\rangle \quad (34)$$

$$= \langle\psi_f|\left(1-\frac{i}{\hbar}L\hat{A}\hat{p}_x\right)e^{i\hat{B}}|\psi_i\rangle \approx \langle\psi_f|e^{i\hat{B}}|\psi_i\rangle\int \langle x|e^{-\frac{i}{\hbar}LA_w\hat{p}_x}|\varphi\rangle|x\rangle dx,$$

or else approximated as:

$$|\Phi\rangle \approx \langle \psi_f | e^{iB} | \psi_i \rangle \int \langle x | \hat{S}(L\, \text{Re}\, A_w) | \phi \rangle |x\rangle\, dx, \quad (35)$$

where:

$$A_w = \frac{\langle \psi_f | \hat{A} e^{iB} | \psi_i \rangle}{\langle \psi_f | e^{iB} | \psi_i \rangle} \quad (36)$$

is the weak value of refraction operator $\hat{A}$. Note that $A_w$ is generally a complex valued quantity. This weak quantity can be calculated directly from theory when $\gamma_\pm$, $\alpha_\pm$, $|\psi_i\rangle$, and $|\psi_f\rangle$ are known. Additionally $n \geq 2$ moments $(\hat{A}^n)_w$ are also defined when $\hat{A}$ is replaced with $\hat{A}^n$ in eqn. (36).

In eqn. (35), use is made of the fact that because $\langle x|\Phi\rangle$ has a real value, then the pointer position must be translated by $L\, \text{Re}\, A_w$. The pointer state distribution in the x-direction then becomes:

$$|\langle x|\Phi\rangle|^2 \approx |\langle \psi_f | e^{iB} | \psi_i \rangle|^2 |\phi(x - L\, \text{Re}\, A_w)|^2, \quad (37)$$

and corresponds to a broad pointer distribution with a single maximum. The distribution's mean can be expressed as:

$$\langle x \rangle = L\, \text{Re}\, A_w. \quad (38)$$

In order for eqn. (35) to be valid, the x-direction Gaussian pointer distribution width $\delta x$ must satisfy both of the following general weakness conditions:

(a) $\delta x \gg L|A_w|$ and (b)

$$\delta x \gg \frac{L}{\min_{(n=2,3,\ldots)} \left|\frac{A_w}{(A^n)_w}\right|^{\frac{1}{n-1}}}. \quad (39)$$

Thus, a precise measurement of the pointer's mean value $\langle x \rangle$ combined with the accurate calculation of $\text{Re}\, A_w$ using eqn. (36) provides the value for thickness $L$ as:

$$L = \frac{\langle x \rangle}{\text{Re}\, A_w} \quad (40)$$

When the above pre- and post-selected states are used, then the weak value of the $n^{th}$ moment of operator $\hat{A}$ in standard form is:

$$(A^n)_w = \frac{aq^* \gamma_+^n (a^*q + b^* r e^{i\eta}) + br^* \gamma_-^n (b^* r + a^* q e^{-i\eta})}{aq^* (a^*q + b^* r e^{i\eta}) + br^* (b^* r + a^* q e^{-i\eta})} \quad (41)$$

where the difference in pre- and post-selection phase angle differences is:

$$\eta = (\alpha_+ - \alpha_-) - (\beta_+ - \beta_-), \quad (42)$$

in which $\alpha_\pm$ represent phase angles induced by the chiral material, and $\beta_\pm$ represents post-selected phase angles.

Now one can choose the first moment n=1 and zero phase angle difference $\eta=0$ in which case:

$$A_w = \frac{aq^* \gamma_+ + br^* \gamma_-}{aq^* + br^*}. \quad (43)$$

One should note that the condition $\eta=0$ corresponds to an extremum for $\text{Re}\, A_w$ with fixed coefficients a, q, b and r. The pre-selection polarizer may be selected so that:

$$a = \sin \Phi \text{ and } b = \cos \Phi, \quad (44)$$

and also the post-selection polarizer so that:

$$q = \cos \chi, \text{ and } r = -\sin \chi. \quad (45)$$

This produces the result:

$$\text{Re}\, A_w = \frac{\gamma_+ \sin\phi \cos\chi - \gamma_- \cos\phi \sin\chi}{\sin(\phi - \chi)}. \quad (46)$$

When conditions include $\Phi \approx \chi$ (i.e., small difference between pre- and post-selection angles) and $\theta_0 \neq 0$ (i.e., non-zero incidence angle), then $|\text{Re}\, A_w|$ can be made arbitrarily large. This means that $\text{Re}\, A_w$ can be used to amplify the shift of the mean position of the pointer state.

In order to clarify by example, let $\Phi = \pi/4$ (such that the pre-selected state is linearly polarized in the x-direction as shown in the diagram 100) and $\chi = \Phi - \epsilon$ (such that the pre- and post-selection coefficients yield approximately similar alignments in relation to the slab's orientation). Then eqn. (43) becomes:

$$A_w = \frac{\gamma_+ (\cos\epsilon + \sin\epsilon) - \gamma_- (\cos\epsilon - \sin\epsilon)}{2\sin\epsilon}, \quad (47)$$

and this weak value $A_w$ can be approximated as:

$$A_w \approx \frac{\gamma_+ - \gamma_- + 2\epsilon\gamma_-}{2\sin\epsilon} \approx \frac{\gamma_+ - \gamma_-}{2\epsilon} \quad (48)$$

when $0 < \epsilon \ll 1$. In this representation, the weak value $A_w$ constitutes a ratio of the refraction translators $\gamma_\pm$ and the pre- and post-selection angle difference $\epsilon$.

In order to show that $\eta=0$ corresponds to an extreme value for fixed a, q, b and r, let n=1. One can assume that a, q, b and r are fixed real valued quantities. Then one can rewrite the real part of eqn. (41) with substituted variables as:

$$\text{Re}\, A_w = \frac{(aq)^2 \gamma_+ + (br)^2 \gamma_- + aqbr(\gamma_+ + \gamma_-)\cos\eta}{(aq)^2 + (br)^2 + 2aqbr\cos\eta} \equiv \frac{X + Y\cos\eta}{V + W\cos\eta}, \quad (49)$$

where the coefficients are defined as $V \equiv (aq)^2 + (br)^2$, $W \equiv 2aqbr$, $X \equiv (aq)^2 \gamma_+ + (br)^2 \gamma_-$, and $Y \equiv aqbr(\gamma_+ + \gamma_-)$.

This result produces first and second derivatives with respective to the phase angle difference $\eta$:

$$\frac{d\text{Re}\, A_w}{d\eta} = \frac{\sin\eta (XW - YV)}{(V + W\cos\eta)^2}, \quad (50)$$

and $$\frac{d^2 \operatorname{Re} A_w}{d\eta^2} = \frac{(XW - YV)(2W + V\cos\eta - W\cos^2\eta)}{(V + W\cos\eta)^3}. \quad (51)$$

Clearly, $d \operatorname{Re} A_w/d\eta=0$ when. As such, this results in the second derivative from eqn. (51) being rewritten as:

$$\frac{d^2 \operatorname{Re} A_w}{d\eta^2} = \frac{(XW - YV)}{(V + W)^2} = (\gamma_+ - \gamma_-)\left[\frac{aqbr(aq - br)}{(aq + br)}\right]. \quad (52)$$

Using the above assignments eqns. (44) and (45) for a, q, b and r yields the second derivative as:

$$\frac{d^2 \operatorname{Re} A_w}{d\eta^2} = -(\gamma_+ - \gamma_-)\left[\frac{\sin\phi\cos\phi\sin\chi\cos\chi\sin(\phi + \chi)}{\sin(\phi - \chi)}\right]. \quad (53)$$

When $\Phi=\pi/4$, i.e., diagonal such that $a=b=\sqrt{2}/2$, and $\chi=\Phi-\epsilon$, then the arguments of all the trigonometric functions in eqn. (53) are first quadrant angles. Because these functions are therefore positive valued, the factor in brackets is a positive quantity so that:

$$\frac{d^2 \operatorname{Re} A_w}{d\eta^2} < 0 \text{ for } (\gamma_+ - \gamma_-) > 0, \quad (54)$$

or else:

$$\frac{d^2 \operatorname{Re} A_w}{d\eta^2} > 0 \text{ for } (\gamma_+ - \gamma_-) < 0. \quad (55)$$

Thus, for $\eta=0$, then $\operatorname{Re} A_w$ is a relative maximum when $(\gamma_+-\gamma_-)$ is greater than zero, or else $\operatorname{Re} A_w$ is a relative minimum when $(\gamma_+-\gamma_-)$ is less than zero. These results are summarized in the following table:

| $\eta$ | $(\gamma_+ - \gamma_-)$ | $\operatorname{Re} A_w$ at $\eta$ |
|---|---|---|
| 0 | >0 | maximum |
|   | <0 | minimum |

At this stage, one can examine inequalities in eqn. (39) in order to establish the appropriate constraint that must be satisfied to ensure that the measurement is weak. One may restrict that $\theta_0$ be small in order that from Snell's law the incident angle exceeds both right and left circular polarization refraction angles $\theta_0 > \theta_\pm$ or alternatively $\theta_0 - \theta_\pm > 0$. Then eqn. (5) yields:

$$\gamma_\pm \approx \theta_0 - \theta_\pm \text{ with } 0 < \gamma_\pm < 1. \quad (56)$$

For the special case of interest, i.e.; when $0<\epsilon\ll 1$, the weakness conditions are:

(a)

$$\delta x \gg L\frac{|\gamma_+ - \gamma_-|}{2\epsilon}$$

and (b) $\delta x \gg L(\gamma_++\gamma_-)$, $\quad$ (57)

where use is made of the fact that:

$$\min_{(n=2,3,\ldots)}\left|\frac{\gamma_+ - \gamma_-}{\gamma_+^n - \gamma_-^n}\right|^{\frac{1}{n-1}} = \left|\frac{\gamma_+ - \gamma_-}{\gamma_+^2 - \gamma_-^2}\right| = (\gamma_+ + \gamma_-)^{-1}, \quad (58)$$

Thus in order that the measurement be weak, one requires that:

$$\delta x \gg L\frac{|\theta_+ - \theta_-|}{2\epsilon}, \quad (59)$$

when $0<\epsilon\ll 1$ and incident angle $\theta_0$ is small.

It can be problematic that the phase angles $\alpha_\pm$ also depend linearly upon the (unknown) thickness L according to:

$$\alpha_\pm = \Delta\alpha_\pm L, \quad (60)$$

where $\Delta\alpha_\pm$ are the specific rotary powers of the slab 110 expressed in radians per unit length and are assumed to be known.

However, the following simple procedure based upon the above analysis can be used to find the post-selected phase angles $\beta_\pm$ that correspond to the condition $\eta=0$. For an apparatus already arranged in position and aligned in the laboratory reference frame using a small known incidence angle $\theta_0$ (i.e., $\theta_0 \le 15°=\pi/12$, the following steps can be performed:

[1] Calculate $\gamma_+$, $\gamma_-$, $(\gamma_+-\gamma_-)$, $(\theta_+-\theta_-)$, choose $0<\epsilon\ll 1$, and verify that condition eqn. (59) is satisfied.

[2] Pre-select $|\psi_i\rangle$ such that alignment coefficients satisfy $a=b=\sqrt{2}/2$.

[3] Post-select $|\psi_f\rangle$ with $$q = \cos\left(\frac{\pi}{4} - \epsilon\right), r = -\sin\left(\frac{\pi}{4} - \epsilon\right),$$

and arbitrary $\beta_\pm$.

[4] Turn on laser.

[5] Vary $\beta_\pm$ until $\langle x \rangle$ is a maximum if $(\gamma_+-\gamma_-)>0$, $\quad$ (61)

or else $\langle x \rangle$ is a minimum if $(\gamma_+-\gamma_-)<0$. $\quad$ (62)

[6] Determine the mean pointer in eqn. (38) as:

$$\langle x \rangle = L \operatorname{Re} A_w = L A_w, \quad (63)$$

based on pointer state distribution $|\langle x|\Phi\rangle|^2$ from eqn. (37).

[7] Turn off laser.

[8] Calculate weak value $\operatorname{Re} A_w = A_w$ using eqn. (47).

[9] Calculate thickness L using eqn. (40).

Note that once $\beta_\pm$ have been determined, then step [5] also provides a value for thickness L. In particular, because $\eta=0$ implies from eqn. (42) that:

$$\alpha_+ - \alpha_- = \beta_+ - \beta_-, \quad (64)$$

then application of eqn. (60) yields:

$$L = \frac{\beta_+ - \beta_-}{\Delta\alpha_+ - \Delta\alpha_-}. \tag{65}$$

This value can be used: (i) as a consistency check for that obtained from step [9]; or (ii) to improve the value for L by averaging.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A method for measuring thickness of a chiral dielectric having parallel ingress and egress surfaces with a normal, said method comprising:
   illuminating a monochromatic coherent polarized light from a laser as an incident beam to the ingress surface at an angle of incidence from the normal;
   polarizing said incident beam at the ingress surface to rotate into first and second circularly polarized beams respectively from the normal by first and second rotation angles;
   polarizing said first and second circularly polarized beams at the egress surface into first and second exit beams parallel to said incident beam respectively separated from said incident beam by first and second displacements;
   measuring said first and second displacements and said first and second rotation angles; and
   determining the thickness of the chiral dielectric based on said first and second rotation angles and said first and second displacements.

2. The method of claim 1, wherein said measuring operation comprises a weak value measurement $A_w$ of a displacement operator of said incident beam.

3. The method of claim 2, wherein said determining operation includes calculating the thickness as $$L = \frac{\langle x \rangle}{\text{Re}A_w},$$

where $\langle x \rangle$ is pointer mean value of said minimum and maximum intensities, and Re $A_w$ is real value of said weak value measurement.

4. The method of claim 1, wherein said illuminating operation comprises emitting single photon pulses of said light.

5. The method of claim 1, wherein the chiral dielectric forms a slab.

6. An apparatus for measuring thickness of a chiral dielectric having parallel ingress and egress surfaces with a normal, said apparatus comprising:
   a laser to emit monochromatic coherent polarized light as an incident beam to the ingress surface at an angle of incidence from the normal, wherein
   said ingress surface polarizes said incident beam to rotate said incident beam into first and second circularly polarized beams respectively from the normal by first and second rotation angles, and
   said egress surface polarizes said first and second circularly polarized beams into first and second exit beams parallel to said incident beam respectively separated from said incident beam by first and second displacements;
   a light-measurement device for measuring said first and second displacements and said first and second rotation angles from said exit beams; and
   a computer processor for determining the thickness of the chiral dielectric based on said first and second rotation angles and said first and second displacements.

7. The apparatus of claim 6, wherein said measurement device provides a weak value measurement $A_w$ of a displacement operator of said exit beams.

8. The apparatus of claim 6, wherein said computer processor calculates the thickness as $$L = \frac{\langle x \rangle}{\text{Re}A_w},$$

where $\langle x \rangle$ is pointer mean value of said minimum and maximum intensities, and Re $A_w$ is real value of said weak value measurement.

9. The apparatus of claim 6, wherein said laser emits single photon pulses for said incident beam.

10. The apparatus of claim 6, wherein the chiral dielectric forms a slab.

11. A method for determining a thickness L of a chiral slab using the slab's refraction of linearly polarized incident light into right (+) and left (−) circular polarized beams, said method comprising:
    disposing the slab in an achiral medium having an established index of refraction $n_0$ with the incident light at a small incidence angle $\theta_0$;
    determining values of translation coefficients $\gamma_\pm$ to establish refraction translation differences ($\gamma_+ - \gamma_-$);
    determining values for refraction angle differences ($\theta_+ - \theta_-$);
    selecting a pre-selection state $|\psi_i\rangle$ such that pre-selection alignment angle satisfies $\Phi = \pi/4$;
    selecting a post-selection state $|\psi_f\rangle$ such that post-selection alignment angle satisfies $\chi = \Phi - \epsilon$ and $0 < \epsilon \ll 1$;
    projecting an emitted light beam through said achiral medium into the chiral slab at an incident angle corresponding to said angle of incidence $\theta_0$;
    varying slab egress phase angles $\beta_\pm$ until pointer mean value $\langle x \rangle$ attains one of a maximum for $(\gamma_+ - \gamma_-) > 0$ or else a minimum for $(\gamma_+ - \gamma_-) < 0$;
    determining said pointer mean value $\langle x \rangle$;
    calculating weak value $$A_w = \frac{\gamma_+(\cos\epsilon + \sin\epsilon) - \gamma_-(\cos\epsilon - \sin\epsilon)}{2\sin\epsilon};$$

and
    calculating the thickness L from said pointer mean value $\langle x \rangle$ and said weak value $A_w$ as $$L = \frac{\langle x \rangle}{\text{Re}A_w}.$$

12. The method according to claim 11, wherein slab induced rotation angles $\alpha_\pm$ and slab egress post-selection angles $\beta_\pm$ represent phase angles such that phase angle difference is $\eta=(\alpha_+-\alpha_-)-(\beta_+-\beta_-)=0$, and the length is expressed as $$L = \frac{\beta_+ - \beta_-}{\Delta\alpha_+ - \Delta\alpha_-}.$$

13. The method according to claim 11, wherein said weak value approximates as $$A_w \approx \frac{\gamma_+ - \gamma_- + 2\varepsilon\gamma_-}{2\sin\varepsilon} \approx \frac{\gamma_+ - \gamma_-}{2\varepsilon}$$

when $0<\varepsilon\ll 1$.

14. A non-volatile computer-readable medium that provides non-transitory instructions for determining a thickness L of a chiral slab using the slab's refraction of linearly polarized incident light into right (+) and left (−) circular polarized beams, said slab being disposed in an achiral medium having an established index of refraction $n_0$ with said incident light at a small incidence angle $\theta_0$, said instructions comprising:

determining values of translation coefficients $\gamma_\pm$ to establish refraction translation differences $(\gamma_+-\gamma_-)$;

determining values for refraction angle differences $(\theta_+-\theta_-)$;

selecting a pre-selection state $|\psi_i\rangle$ such that pre-selection alignment angle satisfies $\Phi=\pi/4$;

selecting a post-selection state $|\psi_f\rangle$ such that post-selection alignment angle satisfies $\chi=\Phi-\epsilon$ and $0<\epsilon\ll 1$;

controlling projection of an emitted light beam through said achiral medium into the chiral slab at an incident angle corresponding to said angle of incidence $\theta_0$;

controlling variation of slab egress phase angles $\beta_\pm$ until pointer mean value $\langle x \rangle$ attains one of a maximum for $(\gamma_+-\gamma_-)>0$ or else a minimum for $(\gamma_+-\gamma_-)<0$;

determining said pointer mean value $\langle x \rangle$;

calculating weak value $$A_w = \frac{\gamma_+(\cos\varepsilon + \sin\varepsilon) - \gamma_-(\cos\varepsilon - \sin\varepsilon)}{2\sin\varepsilon};$$

and calculating the thickness from said pointer mean value $\langle x \rangle$ and said weak value $A_w$ as $$L = \frac{\langle x \rangle}{\mathrm{Re}A_w}.$$

15. The medium according to claim 14, wherein slab induced phase angles $\alpha_\pm$ and slab post-selection egress angles $\beta_\pm$ produce phase angle difference as $\eta=(\alpha_+-\alpha_-)-(\beta_+-\beta_-)=0$, and the length is expressed as $$L = \frac{\beta_+ - \beta_-}{\Delta\alpha_+ - \Delta\alpha_-}.$$

16. The medium according to claim 14, wherein said weak value approximates as $$A_w \approx \frac{\gamma_+ - \gamma_- + 2\varepsilon\gamma_-}{2\sin\varepsilon} \approx \frac{\gamma_+ - \gamma_-}{2\varepsilon}$$

when $0<\epsilon\ll 1$.

* * * * *